(12) United States Patent
Wakabayashi

(10) Patent No.: US 11,160,530 B2
(45) Date of Patent: Nov. 2, 2021

(54) ULTRASONIC TRANSDUCER MODULE, ULTRASONIC ENDOSCOPE AND PROCESSING METHOD OF ULTRASONIC TRANSDUCER MODULE

(71) Applicant: OLYMPUS CORPORATION, Tokyo (JP)

(72) Inventor: Katsuhiro Wakabayashi, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 444 days.

(21) Appl. No.: 16/190,234

(22) Filed: Nov. 14, 2018

(65) Prior Publication Data

US 2019/0117188 A1    Apr. 25, 2019

Related U.S. Application Data

(63) Continuation of application No. PCT/JP2017/017940, filed on May 11, 2017.

(30) Foreign Application Priority Data

May 20, 2016    (JP) .............................. JP2016-101508

(51) Int. Cl.
*A61B 8/12*    (2006.01)
*A61B 8/14*    (2006.01)
(Continued)

(52) U.S. Cl.
CPC ................ *A61B 8/12* (2013.01); *A61B 8/145* (2013.01); *A61B 8/4461* (2013.01); *G01N 29/14* (2013.01); *G01S 7/521* (2013.01); *H04R 17/00* (2013.01)

(58) Field of Classification Search
None
See application file for complete search history.

(56) References Cited

U.S. PATENT DOCUMENTS 5,810,009 A * 9/1998 Mine ..................... B06B 1/0622
310/334
2002/0156373 A1* 10/2002 Wakabayashi ........ B06B 1/0622
600/437
(Continued)

FOREIGN PATENT DOCUMENTS

CN    101237947 A    8/2008
JP    H01-109279 A    4/1989
(Continued)

OTHER PUBLICATIONS

International Search Report dated Aug. 1, 2017 issued in International Application No. PCT/JP2017/017940.
(Continued)

*Primary Examiner* — Yi-Shan Yang
(74) *Attorney, Agent, or Firm* — Scully, Scott, Murphy & Presser, P.C.

(57) ABSTRACT

An ultrasonic transducer module including: a plurality of piezoelectric elements, each being aligned in the same direction that is a longitudinal direction thereof; an electrode formed on a surface of each of the piezoelectric elements; a wiring member configured to be joined with the electrode and electrically connected with the electrode; and a dematching layer provided on a surface of each of the piezoelectric elements, the surface being opposite to another surface of the corresponding piezoelectric element on which the electrode and the wiring member are joined.

7 Claims, 5 Drawing Sheets

(51) Int. Cl.
    *A61B 8/00*           (2006.01)
    *G01N 29/14*         (2006.01)
    *G01S 7/521*          (2006.01)
    *H04R 17/00*        (2006.01)

(56) References Cited

U.S. PATENT DOCUMENTS

| | | | |
|---|---|---|---|
| 2008/0315724 A1* | 12/2008 | Kunkel, III | B06B 1/0633 |
| | | | 310/334 |
| 2009/0062656 A1* | 3/2009 | Hyuga | A61B 8/4488 |
| | | | 600/459 |
| 2015/0263647 A1* | 9/2015 | Watanabe | G01N 29/2418 |
| | | | 73/643 |

FOREIGN PATENT DOCUMENTS

| | | | |
|---|---|---|---|
| JP | H06-177533 A | 6/1994 | |
| JP | H10-223822 A | 8/1998 | |
| JP | H11-056857 A | 3/1999 | |
| JP | 2002-246721 A | 8/2002 | |
| WO | 2015/145296 A1 | 10/2015 | |
| WO | WO-2015145296 A1 * | 10/2015 | ............ B06B 1/0622 |

OTHER PUBLICATIONS

Extended Supplementary European Search Report dated Dec. 18, 2019 in European Patent Application No. 17 79 9285.6.

* cited by examiner

ULTRASONIC TRANSDUCER MODULE, ULTRASONIC ENDOSCOPE AND PROCESSING METHOD OF ULTRASONIC TRANSDUCER MODULE

CROSS-REFERENCE TO RELATED APPLICATION

This application is a continuation of PCT international application Ser. No. PCT/JP2017/017940 filed on May 11, 2017 which designates the United States, incorporated herein by reference, and which claims the benefit of priority from Japanese Patent Applications No. 2016-101508, filed on May 20, 2016, incorporated herein by reference.

BACKGROUND

The present disclosure relates to an ultrasonic transducer module, an ultrasonic endoscope including this ultrasonic transducer at a distal end of an insertion unit, and a processing method of the ultrasonic transducer module.

Ultrasound is applied in some cases for observing a characteristic of a living tissue or material as an observation target. Specifically, an ultrasound observation apparatus performs predetermined signal processing onto an ultrasound echo received from an ultrasonic transducer configured to transmit and receive an ultrasound, whereby information related to the characteristic of the observation target can be obtained.

The ultrasonic transducer includes a plurality of piezoelectric elements that converts an electrical pulse signal into an ultrasound pulse (acoustic pulse), emits the ultrasound pulse to the observation target, converts an ultrasound echo reflected on the observation target into an electrical echo signal, and outputs the echo signal. The ultrasound echo is obtained from the observation target, for example, by arranging the plurality of piezoelectric elements in a predetermined direction and then electronically switching the elements related to transmission and reception.

There is a plurality of types of known ultrasonic transducers having different transmission and reception directions of ultrasound beams, such as convex, linear, and radial types. Among these, the convex ultrasonic transducer includes a plurality of piezoelectric elements arranged along a curved surface, and each of elements emits an ultrasound beam in a radial direction of a curved surface, as disclosed in a Japanese Patent Application No. H1-109279, for example. The Japanese Patent Application No. H1-109279 describes production of a convex ultrasonic transducer by arranging a plurality of piezoelectric elements on a flat surface to connect with a flexible printed circuit (FPC), and thereafter, the plurality of piezoelectric elements is bent to produce the ultrasonic transducer.

SUMMARY

An ultrasonic transducer module according to one aspect of the present disclosure includes: a plurality of piezoelectric elements, each being aligned in the same direction that is a longitudinal direction thereof; an electrode formed on a surface of each of the piezoelectric elements; a wiring member configured to be joined with the electrode and electrically connected with the electrode; and a dematching layer provided on a surface of each of the piezoelectric elements, the surface being opposite to another surface of the corresponding piezoelectric element on which the electrode and the wiring member are joined.

An ultrasonic endoscope according to one aspect of the present disclosure includes an insertion unit that includes the ultrasonic transducer module provided at a distal end of the insertion unit, the insertion unit being configured to be inserted into a subject.

A processing method of an ultrasonic transducer module according to one aspect of the present disclosure includes: a joining step of joining an electrode formed on a surface of individual piezoelectric elements, each being aligned in the same direction that is a longitudinal direction, and a wiring member electrically connected with the electrode; and a dematching layer forming step of forming a dematching layer on a surface of each of the piezoelectric elements, the surface being opposite to another surface of the corresponding piezoelectric element on which the electrode and the wiring member are joined.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
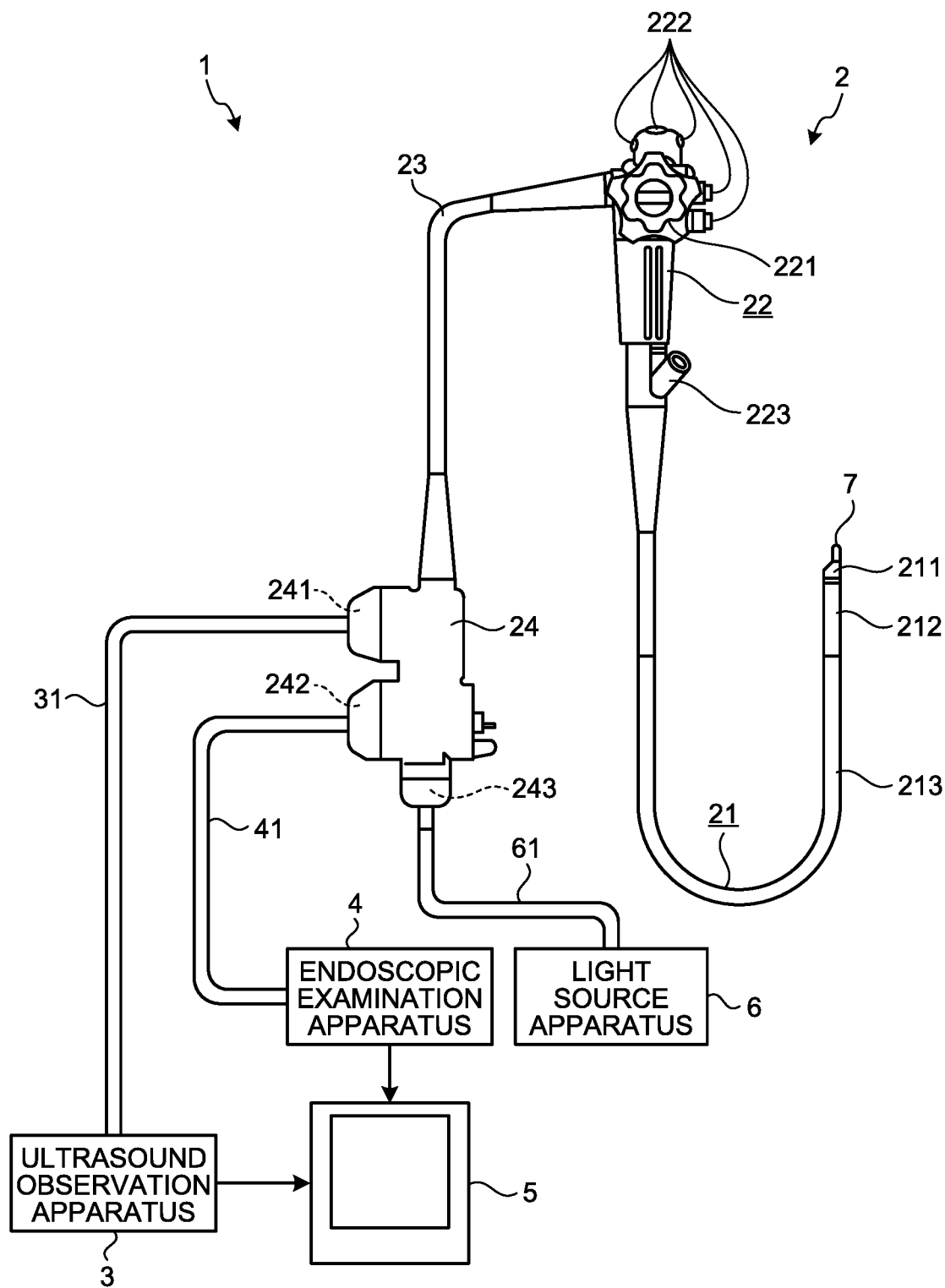
FIG. 1 is a diagram schematically illustrating an endoscope system according to a first embodiment.

Hereinafter, embodiments of the present disclosure (hereinafter, referred to as embodiment(s)) will be described with reference to the drawings. Note that the present disclosure is not limited by the following embodiments. In the drawings, same reference signs are attached to the same portions.

First Embodiment

FIG. 1 is a diagram schematically illustrating an endoscope system according to a first embodiment. An endoscope system 1 is a system for performing ultrasound diagnosis of internal portions of a subject such as a human by using an ultrasonic endoscope. As illustrated in FIG. 1, the endoscope system 1 includes an ultrasonic endoscope 2, an ultrasound observation apparatus 3, an endoscopic examination apparatus 4, a display device 5, and a light source apparatus 6.

The ultrasonic endoscope 2 uses an ultrasonic transducer disposed on a distal end portion to convert an electrical pulse signal transmitted from the ultrasound observation apparatus 3 into an ultrasound pulse (acoustic pulse) and emits it to the subject. The ultrasonic transducer also converts an ultrasound echo reflected on the subject into an electrical echo signal expressed by a voltage change and outputs the signal.

The ultrasonic endoscope 2 typically includes an imaging optical system and image sensors. The ultrasonic endoscope 2 can be inserted into gastrointestinal tracts (esophagus, stomach, duodenum, and large intestine) or respiratory organs (trachea and bronchus) of the subject and can image any of the gastrointestinal tracts and the respiratory organs. Moreover, it is possible to capture their surrounding organs (pancreas, gall bladder, bile duct, biliary tract, lymph nodes, mediastinal organs, blood vessels, or the like) using ultrasound. The ultrasonic endoscope 2 includes a light guide that guides illumination light emitted to the subject at the time of optical imaging. The light guide is configured such that a distal end portion thereof reaches a distal end of an insertion unit of the ultrasonic endoscope 2 into the subject, while a proximal end portion thereof is connected to the light source apparatus 6 that generates illumination light.

As illustrated in FIG. 1, the ultrasonic endoscope 2 includes an insertion unit 21, an operating unit 22, a universal cord 23, and a connector 24. The insertion unit 21 is a portion to be inserted into the subject. As illustrated in FIG. 1, the insertion unit 21 includes: a rigid distal end portion 211 provided on a distal end side to hold an ultrasonic transducer 7; a bending portion 212 coupled to the proximal end side of the distal end portion 211 and configured to be bendable; and a flexible tube portion 213 having flexibility and coupled to the proximal end side of the bending portion 212. Although not specifically illustrated herein, the insertion unit 21 internally includes: a light guide that transmits illumination light supplied from the light source apparatus 6; a plurality of signal cables for transmitting various signals; and a treatment instrument insertion passage for inserting treatment instruments.

The ultrasonic transducer 7 is a convex ultrasonic transducer having a plurality of piezoelectric elements arranged in an array for electronically switching piezoelectric elements related to transmission and reception or delaying transmission and reception of each of the piezoelectric elements to perform electronic scanning. The configuration of the ultrasonic transducer 7 will be described below.

Figure 2:
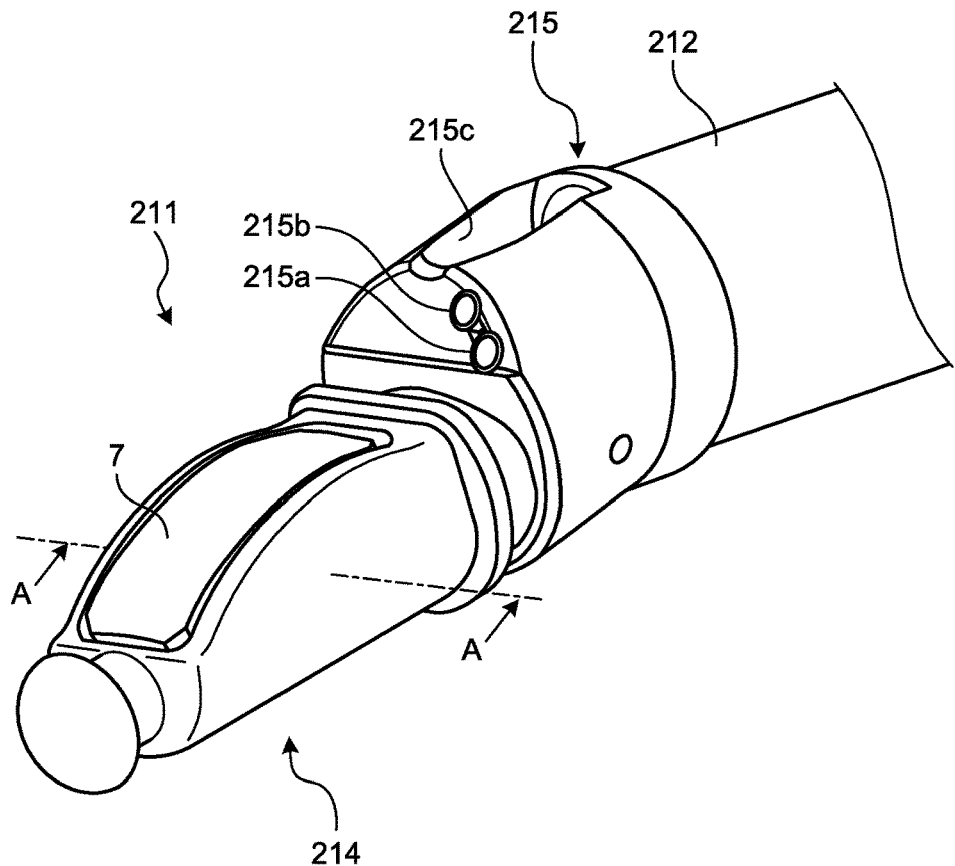
FIG. 2 is a perspective view schematically illustrating a configuration of a distal end of an insertion unit of an ultrasonic endoscope according to the first embodiment.

FIG. 2 is a perspective view schematically illustrating a configuration of a distal end of an insertion unit of an ultrasonic endoscope according to the first embodiment. As illustrated in FIG. 2, the distal end portion 211 includes an ultrasonic transducer module 214 that holds the ultrasonic transducer 7; an illumination lens 215a that converges the illumination light and emits the illumination light to the outside; and an endoscope module 215 including an objective lens 215b constituting the imaging optical system for capturing external light. The endoscope module 215 includes a treatment instrument protrusion port 215c communicating with a treatment instrument insertion passage formed in the insertion unit 21 to allow the treatment instrument to protrude from the distal end of the insertion unit 21. The treatment instrument insertion passage is provided to allow the vicinity of an end portion connected to the treatment instrument protrusion port 215c to be inclined with respect to the longitudinal axis of the insertion unit 21 and allow the treatment instrument to protrude from the treatment instrument protrusion port 215c in a direction inclined with respect to the longitudinal axis. Here, the longitudinal axis is an axis along the longitudinal direction of the insertion unit 21. While the axial direction varies depending on individual positions in the bending portion 212 and the flexible tube portion 213, the longitudinal axis of the rigid distal end portion 211 is a constant linear axis.

The operating unit 22 is coupled to the proximal end side of the insertion unit 21 and receives various types of operation from a user such as a doctor. As illustrated in FIG. 1, the operating unit 22 includes: a bending knob 221 for performing bending operation on the bending portion 212; and a plurality of operating members 222 for performing various types of operation. Moreover, the operating unit 22 has a treatment instrument insertion port 223 communicating with the treatment instrument insertion passage to be used for inserting treatment instruments into the treatment instrument insertion passage.

The universal cord 23 is a cable extending from the operating unit 22 and including a plurality of signal cables for transmitting various signals and an optical fiber for transmitting illumination light supplied from the light source apparatus 6.

The connector 24 is provided at the distal end of the universal cord 23. The connector 24 includes first to third connector units 241 to 243 each of which is connected with an ultrasound cable 31, a video cable 41, and an optical fiber cable 61, respectively.

The ultrasound observation apparatus 3 is electrically connected with the ultrasonic endoscope 2 via the ultrasound cable 31 (FIG. 1), outputs a pulse signal to the ultrasonic endoscope 2 via the ultrasound cable 31, while inputting echo signals from the ultrasonic endoscope 2. The ultrasound observation apparatus 3 subsequently performs predetermined processing on the echo signal and generates an ultrasound image.

The endoscopic examination apparatus 4 is electrically connected with the ultrasonic endoscope 2 via the video cable 41 (FIG. 1), and inputs an image signal from the ultrasonic endoscope 2 via the video cable 41. The endoscopic examination apparatus 4 subsequently performs predetermined processing on the image signal and generates an endoscopic image.

The display device 5 is formed with liquid crystal, organic electroluminescence (EL), a projector, a cathode ray tube (CRT), or the like, and displays an ultrasound image generated by the ultrasound observation apparatus 3, an endoscopic image generated by the endoscopic examination apparatus 4, or the like.

The light source apparatus 6 is connected with the ultrasonic endoscope 2 via the optical fiber cable 61 (FIG. 1) and supplies illumination light for illuminating portions inside the subject, to the ultrasonic endoscope 2 via the optical fiber cable 61.

Figure 3:
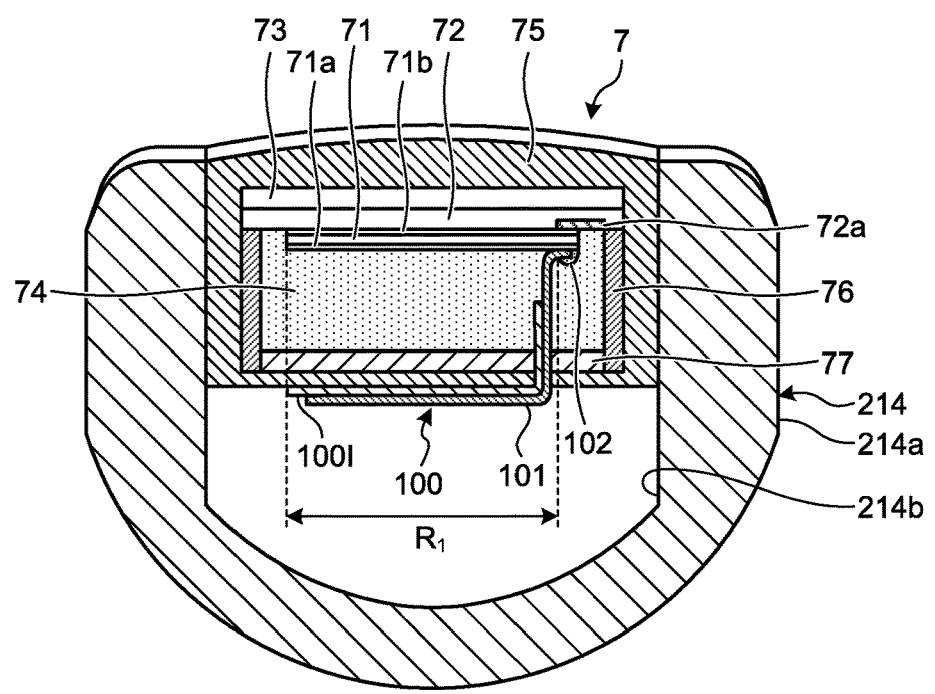
FIG. 3 is a partial cross-sectional view corresponding to line A-A illustrated in FIG. 2.

Subsequently, a configuration of the ultrasonic transducer 7 provided at the distal end of the insertion unit 21 will be described with reference to FIGS. 2 to 5. FIG. 3 is a partial cross-sectional view corresponding to line A-A illustrated in FIG. 2. The first embodiment is described as an exemplary case where the ultrasonic transducer 7 is a convex ultrasonic transducer as illustrated in FIG. 2 including a one-dimensional array (1D array) of the plurality of piezoelectric elements 71 arranged in a line. In other words, in the ultrasonic transducer 7 according to the first embodiment, the plurality of piezoelectric elements 71 is arranged along the outer surface forming the curved surface of the ultrasonic transducer 7, and transmits and receives ultrasound on a plane including the longitudinal axis and parallel to the longitudinal axis.

The ultrasonic transducer 7 includes: a plurality of piezoelectric elements 71 having a prismatic shape and each being aligned in the same direction that is the longitudinal direction thereof; a first acoustic matching layer 72 provided on an outer surface side of the ultrasonic transducer 7 with respect to the piezoelectric element 71; a second acoustic matching layer 73 provided on the side on the first acoustic matching layer 72 opposite to the side coming in contact with the piezoelectric element 71; a backing material 74 provided on the side on the piezoelectric element 71 opposite to the side coming in contact with the first acoustic matching layer 72; and an acoustic lens 75 provided on a side on the second acoustic matching layer 73 opposite to the side coming in contact with the first acoustic matching layer 72. The backing material 74 is filled in a hollow space formed by the piezoelectric element 71, the first acoustic matching layer 72, a wall portion 76 erected on the side on the first acoustic matching layer 72 on which the piezoelectric element 71 is disposed, and a lid portion 77 formed with a hard resin to seal one end side of the wall portion 76. The acoustic lens 75 covers outer surfaces of the first acoustic matching layer 72, the second acoustic matching layer 73, the wall portion 76, and the lid portion 77. The acoustic lens 75 forms the outer surface of the ultrasonic transducer 7.

The piezoelectric element 71 converts an electrical pulse signal into an acoustic pulse, emits this pulse to the subject, converts an ultrasound echo reflected on the subject into an electrical echo signal expressed by a voltage change, and outputs the echo signal. On the piezoelectric element 71, a signal input/output electrode 71a is provided on a backing material 74-side main surface, and a ground electrode 71b for grounding is provided on a first acoustic matching layer 72-side main surface of the piezoelectric element 71. Each of the electrodes is formed using a metal material or a resin material, having conductivity. The main surface herein refers to an acoustic radiation surface and a surface facing the acoustic radiation surface. The surface continuous with the main surface is referred to as a side surface.

In order to allow the sound (ultrasound) to be efficiently transmitted between the piezoelectric element 71 and an observation target, the first acoustic matching layer 72 and the second acoustic matching layer 73 perform matching of acoustic impedance of the piezoelectric element 71 and the acoustic impedance of the observation target. The first acoustic matching layer 72 and the second acoustic matching layer 73 are formed of mutually different materials. Note that while the first embodiment describes a case where there are two acoustic matching layers (first acoustic matching layer 72 and second acoustic matching layer 73), it is also allowable to have one layer or three layers or more, in accordance with characteristics of the piezoelectric element 71 and the observation target.

The first acoustic matching layer 72 includes a ground electrode 72a electrically connected to the ground electrode 71b of the piezoelectric element 71. The ground electrode 72a is formed of a conductive material having higher conductivity than the acoustic impedance of the piezoelectric element 71 and functions as a dematching layer. The piezoelectric element 71 is grounded to the outside via the ground electrode 72a.

The backing material 74 attenuates unnecessary ultrasound vibration generated by operation of the piezoelectric element 71. The backing material 74 is formed of a material having a high attenuation rate, for example, epoxy resin in which a filler such as alumina and zirconia is dispersed, or formed of a rubber in which the above-described filler is dispersed.

The acoustic lens 75 is formed with silicone, polymethylpentene, epoxy resin, polyetherimide, or the like. One of the surfaces of the acoustic lens 75 is formed into a protruding or recessed shape, leading to a function of narrowing the ultrasound, thereby emitting the ultrasound that passes through the second acoustic matching layer 73 to the outside, or incorporating an ultrasound echo from the outside. Whether to provide the acoustic lens 75 may be optional, and thus, it is allowable to have a configuration without the acoustic lens 75.

The piezoelectric element 71 vibrates with an input of a pulse signal, whereby the above-configured ultrasonic transducer 7 emits ultrasound to the observation target via the first acoustic matching layer 72, the second acoustic matching layer 73, and the acoustic lens 75. At this time, the piezoelectric element 71 is configured such that the backing material 74 attenuates unnecessary vibration of the piezoelectric element 71 on the opposite side of the arrangement side of the first acoustic matching layer 72, the second acoustic matching layer 73, and the acoustic lens 75. Moreover, the ultrasound reflected from the observation target is transmitted to the piezoelectric element 71 via the acoustic lens 75, the second acoustic matching layer 73, and the first acoustic matching layer 72. The transmitted ultrasound causes the piezoelectric element 71 to vibrate, and then, the piezoelectric element 71 converts the vibration into an electrical echo signal, and outputs the echo signal to the ultrasound observation apparatus 3 via a wiring member 101 described below.

As illustrated in FIG. 3, the ultrasonic transducer module 214 has a housing 214a in which a housing hole 214b capable of housing the ultrasonic transducer 7 and a relay substrate 100 described later is formed.

The ultrasonic transducer module 214 includes a relay substrate 100 that relays electrical connection between the ultrasonic transducer 7 and a cable forming a part of a path for electrically connecting the ultrasonic transducer 7 (ultrasonic transducer module 214) to the ultrasound observation apparatus 3. The relay substrate 100 includes: an insulating member 1001 being a flexible printed circuit (FPC) held by the ultrasonic transducer 7 on one end side of the ultrasonic transducer 7 and on the side opposite to the surface used for transmitting/receiving ultrasound; and a wiring member 101 which is a conductive member extending in a flying lead structure so as to be electrically connected to the signal input/output electrode 71a. The insulating member 1001 is formed with an insulating material such as polyimide. A plurality of the wiring members 101 is provided corresponding to the number of the piezoelectric elements 71 to be connected. A part of the plurality of wiring members 101 may be integrated at a portion where the insulating member 1001 is provided.

The wiring member 101 is formed with a conductive material such as nickel, copper, or an alloy containing nickel or copper as a main component. An end portion of the wiring member 101 on the side connected to the signal input/output electrode 71a is curved to form an L-shape. The wiring member 101 is positioned in an area extending in a stacking direction of the piezoelectric element 71, the first acoustic matching layer 72 and the second acoustic matching layer 73, being an area $R_1$ that passes through a matching layer of the piezoelectric element 71. The term "matching layer" as used herein refers to a portion of the first acoustic matching layer 72 and the second acoustic matching layer 73 that allow the ultrasound from the piezoelectric element 71 to pass, being a layer formed by a portion excluding a dematching layer formed by the ground electrode 71b or the like. Ultrasound and the above-described unnecessary vibration are also transmitted from the piezoelectric element 71 to the backing material 74 side of this area $R_1$, and the ultrasound transmitted as unnecessary vibration is attenuated by the backing material 74.

The signal input/output electrode 71a and the wiring member 101 are joined with each other by a joint 102. The joint 102 is an electrolytic plating layer formed by an electrolytic plating method using a conductive material such as nickel, copper, or an alloy containing nickel or copper as a main component. The electrolytic plating method controls voltage or time so as to perform quantitative control of the material forming the joint 102. Note that the joint 102 may be formed by a molten solder method.

Here, it is preferable that a joining portion on the piezoelectric element 71 with the joint 102 is a piezoelectrically inactive area in order to accurately transmit and receive ultrasound. Being piezoelectrically inactive means that it is not polarized or that no electric field is applied.

Figure 4:
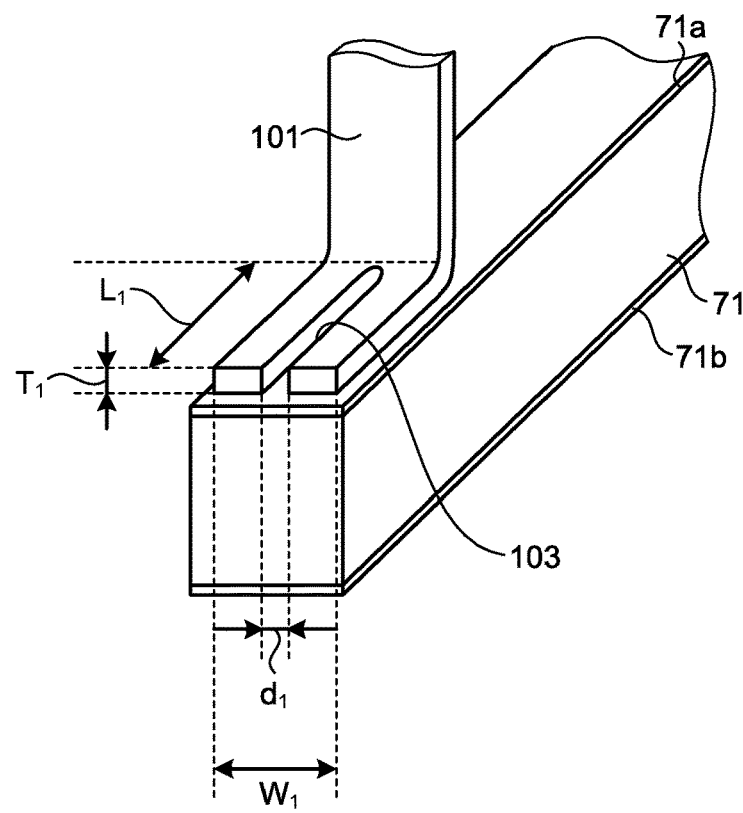
FIG. 4 is a schematic diagram illustrating a configuration of a main portion of an ultrasonic transducer module according to the first embodiment, being a schematic diagram illustrating a configuration of a wiring member.

FIG. 4 is a schematic diagram illustrating a configuration of a main portion of an ultrasonic transducer module according to the first embodiment, being a schematic diagram illustrating a configuration of a wiring member. The wiring member 101 extends from the relay substrate 100 so as to have a bent distal end. A recess 103 is formed at distal end of the wiring member 101. The recess 103 has a notch shape cut out from the distal end of the wiring member 101 along the longitudinal direction of the wiring member 101. A joining area with the joint 102 includes this recess 103.

In the joining area on the wiring member 101 with the joint 102, in a case where a length in the longitudinal direction of the wiring member 101 is $L_1$, a thickness of the wiring member 101 is $T_1$, a length in the short direction of the wiring member 101 is $W_1$, and a groove width of notch in the recess 103 is $d_1$, $T_1 > d_1$ is satisfied. The contact area on the wiring member 101 with the joint 102, namely, a surface area $S_1$ on the wiring member 101 to be joined with the joint 102 is expressed by:

$$S_1 = ((W_1 - d_1)/2 + T_1) \times L_1 \times 4 + \{(W_1 - d_1)/2\} \times T_1 \times 2.$$

Figure 5:
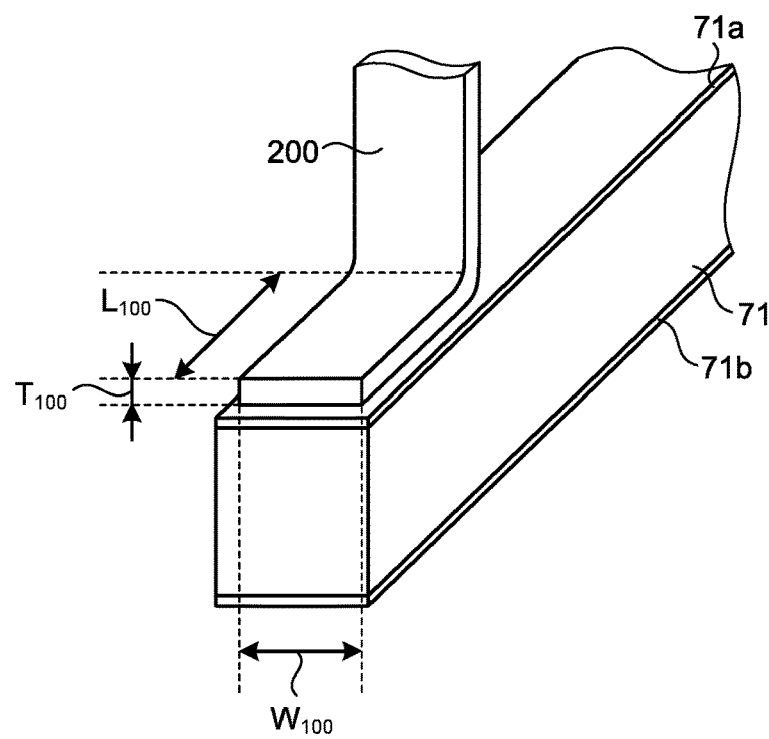
FIG. 5 is a schematic diagram illustrating a configuration of a main portion of a conventional ultrasonic transducer module, being a schematic diagram illustrating a configuration of a wiring member.

FIG. 5 is a schematic diagram illustrating a configuration of a main portion of a conventional ultrasonic transducer module, being a schematic diagram illustrating a configuration of a wiring member. A conventional wiring member 200 without the recess 103 extends from an insulating member 1001 so as to have a bend distal end. Hereinafter, it is assumed that the signal input/output electrode 71a and the wiring member 200 are joined by the joint 102.

In the joining area on the wiring member 200 with the joint 102, in a case where a length in the longitudinal direction of the wiring member 200 is $L_{100}$, a thickness of the wiring member 200 is $T_{100}$, and a length in the short direction of the wiring member 200 is $W_{100}$, the contact area on the wiring member 200 with the joint 102, namely, a surface area $S_{100}$ on the wiring member 200 to be joined with the joint 102 is expressed by:

$$S_{100} = (W_{100} + T_{100}) \times L_{100} \times 2 + W_{100} \times T_{100}.$$

For example, in a case where the lengths $L_1$ and $L_{100}$ are 300 (μm), the thicknesses $T_1$ and $T_{100}$ are 25 (μm), the lengths $W_1$ and $W_{100}$ are 70 (μm), and the groove width $d_1$ is 10 (μm), the surface area ratio $S_1:S_{100}$ is 115:100. This indicates that the wiring member 101 according to the first embodiment has a larger surface area. This leads to the larger joining area of the wiring member 101 when being joined with the joint 102 than the joining area of the conventional wiring member 200, making it possible to improve the joining strength.

Subsequently, a processing method of the above-described ultrasonic transducer module 214 will be described. A first step of manufacturing the ultrasonic transducer module 214 is to stack the first acoustic matching layer 72 and the second acoustic matching layer 73 on the piezoelectric element 71. At this time, the ground electrode 71b in the piezoelectric element 71 comes in contact with the ground electrode 72a in the first acoustic matching layer 72.

Thereafter, the signal input/output electrode 71a and the wiring member 101 are joined with each other at the joint 102 (joining step) in a state where the signal input/output electrode 71a of the piezoelectric element 71 and the wiring member 101 are in contact with each other. The joint 102 is formed by the above-described electrolytic plating method, for example. The use of the electrolytic plating method makes it possible to suppress the generation of heat when joining the signal input/output electrode 71a with the wiring member 101 as compared with the conventional soldering, enabling suppression of thermal deterioration of the piezoelectric element 71. In addition, the electrolytic plating method can be used to collectively join a plurality of pairs of the signal input/output electrodes 71a and the wiring members 101, enabling reduction of the manufacturing cost. The joint 102 may be formed by a molten solder method.

Note that the manufacturing order described above may be reversed. Specifically, the signal input/output electrode 71a and the wiring member 101 may be joined to each other first, and then, the first acoustic matching layer 72 and the second acoustic matching layer 73 may be stacked on the piezoelectric element 71.

The first acoustic matching layer 72 and the second acoustic matching layer 73 are first stacked on the piezoelectric element 71 and next the wiring member 101 is joined to the signal input/output electrode 71a, and then, the wall portion 76 is erected on the first acoustic matching layer 72. Thereafter, the liquid backing material 74 is cast using the wall portion 76 as an ingate and cured. When casting and curing the backing material 74, the relay substrate 100 is placed at a desired position. Thereafter, the lid portion 77 is formed on the backing material 74 by using an epoxy resin, for example. Note that although FIG. 3 illustrates two wall portions 76 alone, another wall portion may also be formed on the end portion side of the arranged piezoelectric element 71 to form a frame.

Thereafter, the acoustic lens 75 is attached to the outer peripheries of the first acoustic matching layer 72, the second acoustic matching layer 73, the wall portion 76, and the lid portion 77. Furthermore, the acoustic lens 75 is attached to the housing 214a. With this processing, the ultrasonic transducer module 214 illustrated in FIG. 3 is manufactured.

According to the first embodiment described above, the recess 103 is formed in the joining area on the wiring member 101 in the process of joining, at the joint 102, the signal input/output electrode 71a of the piezoelectric element 71 with the wiring member 101 extending from the relay substrate 100. According to the first embodiment, it is possible to increase the joining area on the wiring member 101 with the joint 102 compared with the case of the wiring member 200 without the recess 103, making it possible to ensure the joining strength between the piezoelectric element and the wiring even in a case where the pitch is reduced. With this configuration, it is possible to improve the durability of the connection between the piezoelectric element and the wiring.

Furthermore, according to the above-described first embodiment, the groove width $d_1$ of the recess 103 is made smaller than the thickness $T_1$ of the wiring member 101. This increases the contact area between the wiring member 101 and the joint 102 compared with the conventional configuration, making it possible to improve the joining strength between the piezoelectric element and the wiring.

Moreover, according to the above-described first embodiment, forming the recess 103 can reduce the weight of the wiring member 101 as compared with the conventional configuration, making it possible to reduce unnecessary vibration, leading to improvement of the image quality of the obtained image.

In the first embodiment described above, the recess 103 is described as having a notch shape cut out from the distal end of the wiring member 101 along the longitudinal direction of the wiring member 101. The shape of the recess, however, is not limited to this shape. For example, the shape may be different from the notch shape according to the first embodiment, or it is allowable to increase the surface area by using porous material. Hereinafter, other examples of recesses will be described in first to third modifications.

First Modification of the First Embodiment

Figure 6:
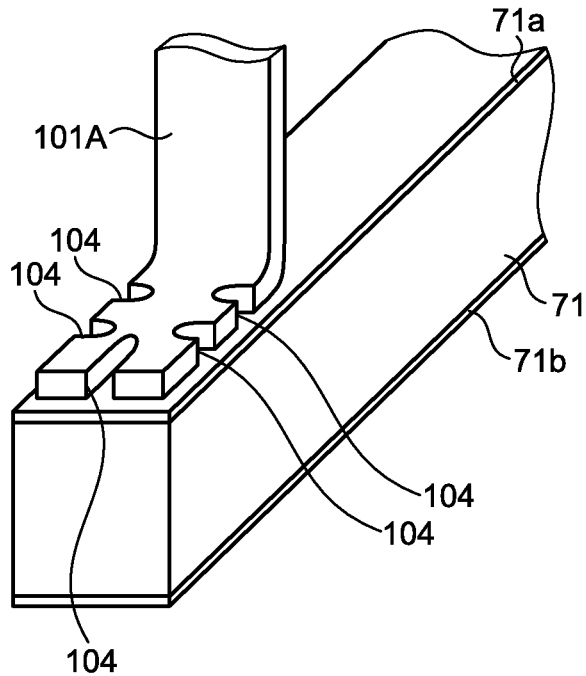
FIG. 6 is a schematic diagram illustrating a configuration of a main portion of an ultrasonic transducer module according to a first modification of the first embodiment, being a schematic diagram illustrating a configuration of a wiring member.

FIG. 6 is a schematic diagram illustrating a configuration of a main portion of an ultrasonic transducer module according to a first modification of the first embodiment, being a schematic diagram illustrating a configuration of a wiring member. A wiring member 101A illustrated in FIG. 6 includes a plurality of recesses 104 cut out from the side surface of the wiring member 101A. Each of the recesses 104 extends in a direction parallel or perpendicular to the extending direction of the wiring member 101A. With the first modification, it is also possible to increase the joining area with the joint 102 as compared with the conventional case.

Second Modification of the First Embodiment

Figure 7:
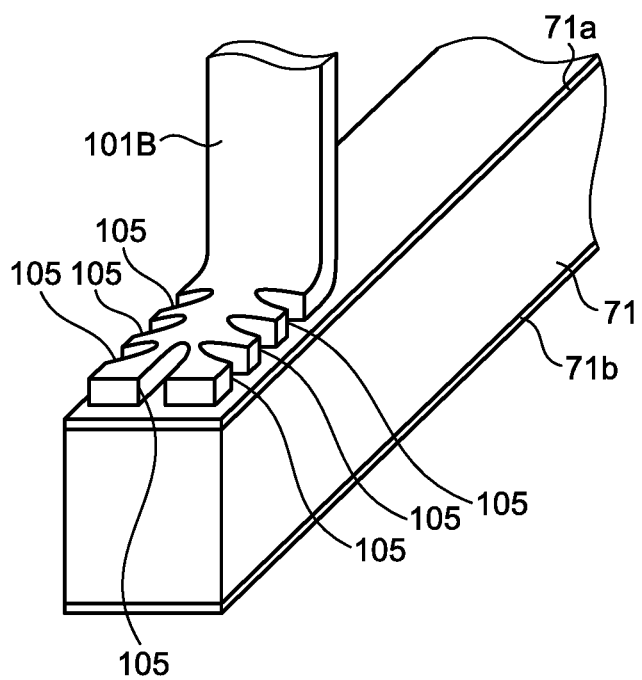
FIG. 7 is a schematic diagram illustrating a configuration of a main portion of an ultrasonic transducer module according to a second modification of the first embodiment, being a schematic diagram illustrating a configuration of a wiring member.

FIG. 7 is a schematic diagram illustrating a configuration of a main portion of an ultrasonic transducer module according to a second modification of the first embodiment, being a schematic diagram illustrating a configuration of a wiring member. A wiring member 101B illustrated in FIG. 7 includes a plurality of recesses 105 cut out from the side surface of the wiring member 101B. Each of the recesses 105 extends in a direction parallel to the extending direction of the wiring member 101B, or extends in a direction inclined with respect to a direction orthogonal to the extending direction. With the second modification, it is also possible to increase the joining area with the joint 102 as compared with the conventional case.

Third Modification of the First Embodiment

Figure 8:
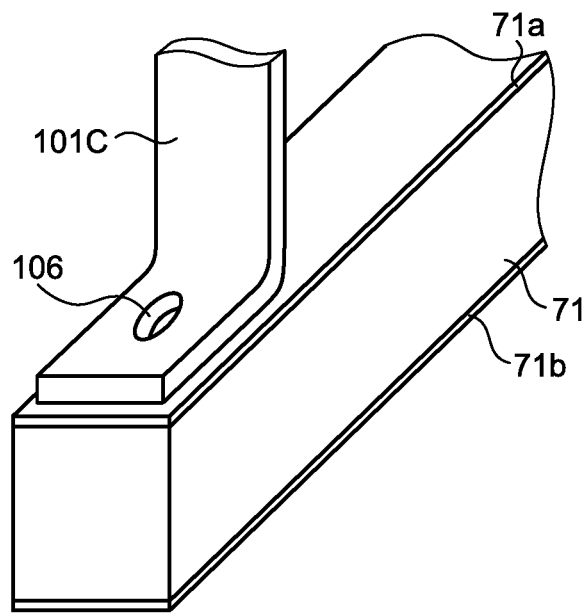
FIG. 8 is a schematic diagram illustrating a configuration of a main portion of an ultrasonic transducer module according to a third modification of the first embodiment, being a schematic diagram illustrating a configuration of a wiring member.

FIG. 8 is a schematic diagram illustrating a configuration of a main portion of an ultrasonic transducer module according to a third modification of the first embodiment, being a schematic diagram illustrating a configuration of a wiring member. A wiring member 101C illustrated in FIG. 8 includes a recess 106 having a hole shape penetrating from one main surface to the other main surface of opposing main surfaces of the wiring member 101C. With the third modification, the surface area is increased by the inner peripheral surface of the recess 106, also making it possible to increase the joining area with the joint 102 as compared with the conventional case.

Second Embodiment

Figure 9:
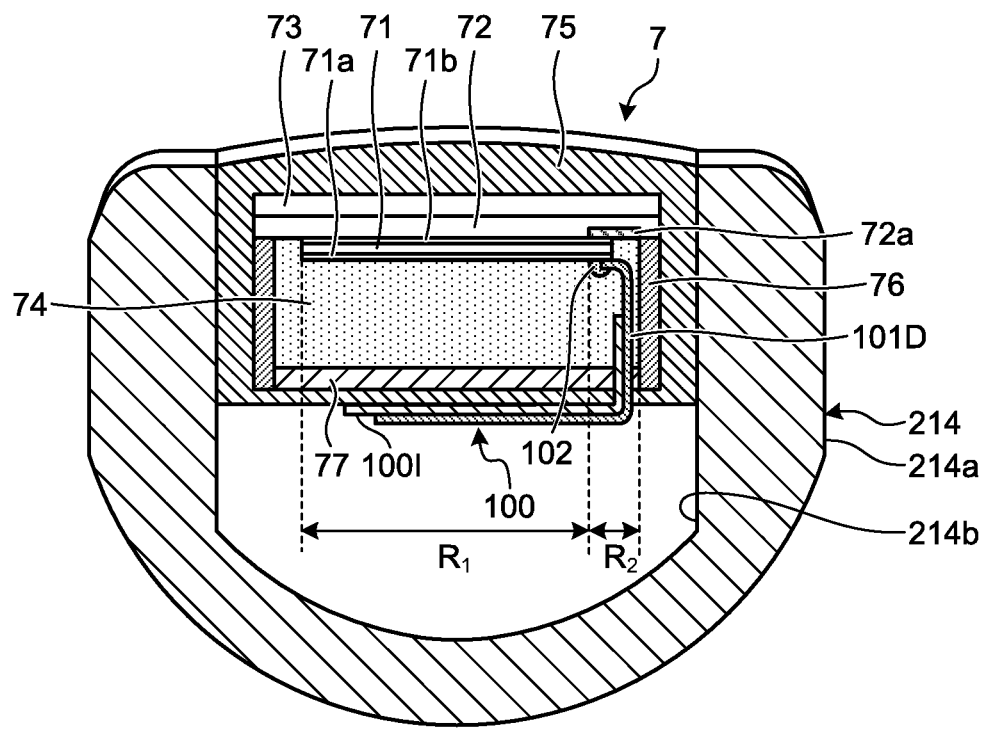
FIG. 9 is a schematic diagram illustrating a configuration of a main portion of an ultrasonic transducer module according to a second embodiment, being a schematic diagram illustrating a configuration of a wiring member.

FIG. 9 is a schematic diagram illustrating a configuration of a main portion of an ultrasonic transducer module according to a second embodiment, being a schematic diagram illustrating a configuration of a wiring member. In the above-described first embodiment, the wiring member 101 is located inside the area $R_1$ that passes through the matching layer of the piezoelectric element 71. In the second embodiment, however, a wiring member 101D is arranged in an area $R_2$ extending in the stacking direction of the piezoelectric element 71, the first acoustic matching layer 72, and the second acoustic matching layer 73, that is, the area $R_2$ being the area that corresponds to a dematching layer formed by the ground electrode 72a and suppressing the passing of the ultrasound from the piezoelectric element 71, and in the area $R_2$ not including the piezoelectric element 71.

Ultrasound is transmitted from the piezoelectric element 71 to the matching layer. Accordingly, when a wiring material exists in an area passing through the matching layer, the ultrasound would be reflected on the wiring member toward the piezoelectric element 71 side, leading to reception of an unnecessary ultrasound echo by the piezoelectric element 71 in some cases. In the second embodiment, as illustrated in FIG. 9, the wiring member 101D is arranged in the area $R_2$ passing through the dematching layer so as to suppress the reception of unnecessary ultrasound echo by the piezoelectric element 71. In addition, disposing a matching layer on a surface opposite to the joining portion with the joint 102 might cause disturbance in the sound field due to the addition of the joint 102. By adopting the above-described arrangement, however, it is possible to suppress the disturbance of the sound field, leading to improvement of the image quality of the obtained image.

Similarly to the above-described first embodiment, according to the second embodiment described above, the recess 103 is formed in the joining area on the wiring member 101D in the process of joining, at the joint 102, the signal input/output electrode 71a of the piezoelectric element 71 with the wiring member 101D extending as a flying lead structure from the relay substrate 100. According to the second embodiment, it is possible to increase the joining area on the wiring member 101D with the joint 102 compared with the case of the wiring member 200 without the recess 103, making it possible to ensure the joining strength between the piezoelectric element and the wiring even in a case where the pitch is reduced.

In addition, according to the second embodiment, the wiring member 101D is positioned within the area $R_2$ corresponding to the dematching layer. This configuration suppresses incidence of the ultrasound reflected on the wiring member 101D onto the piezoelectric element 71 of the matching layer, making it possible to suppress reception of an unnecessary ultrasound echo by the piezoelectric element 71. This makes it possible to suppress noise due to unnecessary ultrasound echo and to improve the image quality of the ultrasound image obtained by the ultrasonic transducer 7.

Note that while the above-described second embodiment is a case where the wiring member 101D is disposed in an area corresponding to the dematching layer through which the ultrasound from the piezoelectric element 71 would not pass and in an area not including the piezoelectric element 71, it is sufficient as long as the wiring member 101D is arranged in either one of the areas. Specifically, the wiring member 101D may be disposed in an area corresponding to the dematching layer through which the ultrasound from the piezoelectric element 71 would not pass, or may be arranged in an area not including the piezoelectric element 71.

While embodiments of the present disclosure have been described hereinabove, the present disclosure is not intended to be limited to the above-described embodiments and the modifications. The present disclosure is not intended to be limited to the above-described embodiments and modifications but may include various forms of embodiments without deviating from the technical spirit and scope of the general inventive concept as defined in the appended claims of this disclosure. Furthermore, the components described in each of the embodiments and modifications may be appropriately combined with each other.

Moreover, while the above-described first and second embodiments are cases where the recess has a groove shape in which a part of the wiring member is cut out so as to penetrate the opposing main surfaces, the recess may have a bottomed groove shape. The recess may have a bottomed groove shape or a recessed shape, or may have a groove shape or a hole shape not having a bottom. In addition, the surface roughness of the wiring member may be increased to increase the surface area, or the above-described bottomed groove shape and the groove shape not having the bottom may be combined with each other.

While the above-described first and second embodiments are exemplary cases where the cross section having the plane orthogonal to the extending direction of the wiring member as a section has a rectangular shape, the present disclosure is not limited to this and the shape may be trapezoidal. The shape of the wiring member can be appropriately designed corresponding to the way of cutting at the time of forming the recess.

While the above-described first and second embodiments are cases where the recesses are provided in the wiring member and the wiring member and the electrode are joined with each other on the joint 102. Alternatively, however, the wiring member and the electrode may be joined to each other by using the molten solder method.

Moreover, the above-described first and second embodiments are exemplary cases where a piezoelectric element is used for emitting ultrasound and converting the ultrasound incident from the outside into an echo signal. The present disclosure, however, is not limited to this, and may use a device utilizing Micro Electro Mechanical Systems (MEMS), such as Capacitive Micromachined Ultrasonic Transducers (C-MUT) or Piezoelectric Micromachined Ultrasonic Transducers (P-MUT), for example.

Furthermore, it is allowable to apply the present technique as an ultrasonic endoscope to a small-diameter ultrasound probe not including an optical system and configured to perform scanning by mechanically rotating the transducer. In typical cases, the ultrasound miniature probe is inserted into biliary tract, bile duct, pancreatic duct, trachea, bronchus, urethra, and ureter, and is applicable to the examination of the surrounding organs (pancreas, lung, prostate gland, bladder, lymph nodes, and the like).

The ultrasonic transducer may be any of a linear transducer, radial transducer, and a convex transducer. In a case where the ultrasonic transducer is a linear transducer, the scanning area has a quadrangular shape (rectangle or square). In a case where the ultrasonic transducer is a radial transducer or a convex transducer, the scanning area is fan-shaped or circular. The ultrasonic endoscope may cause the ultrasonic transducer to perform mechanical scan, or may provide, as the ultrasonic transducer, a plurality of elements in an array, and may cause the ultrasonic transducer to perform electronic scan by electronically switching elements related to transmission/reception or imposing delay onto transmission/reception of each of elements.

Moreover, although an example is described as an ultrasonic endoscope, the ultrasonic transducer module of the present disclosure may be applied to an external ultrasound probe that emits ultrasound from a body surface of a subject. The external ultrasound probe is typically used to examine abdominal organs (liver, gall bladder, and bladder), breast (mammary gland, in particular), and the thyroid.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic transducer module comprising:
   a plurality of piezoelectric elements, each being aligned in a longitudinal direction;
   an electrode formed on a first surface of each of the plurality of piezoelectric elements;
   a wiring member configured to be joined with the electrode and electrically connected with the electrode;
   a recess provided at a joining area on the wiring member, wherein the wiring member is joined with the electrode at the joining area; and
   a dematching layer provided on a second surface of each of the plurality of piezoelectric elements, each second surface faces the first surface and is opposite to the first surface on which the electrode and the wiring member are joined.

2. The ultrasonic transducer module according to claim 1, wherein
   the recess has a groove shape that is formed by cutting out part of one end of the wiring member, and
   a groove width of the recess being smaller than a thickness of the wiring member.

3. The ultrasonic transducer module according to claim 1, further comprising a joint configured to join the electrode and the wiring member,
   wherein the joint is an electrolytic plating layer formed by using a metal containing nickel or copper.

4. The ultrasonic transducer module according to claim 1, wherein the plurality of piezoelectric elements are arranged along a curved surface.

5. An ultrasonic endoscope, comprising:
   an insertion unit configured to be inserted into a subject;
   an ultrasonic transducer module provided at a distal end of the insertion unit, the ultrasonic transducer module comprising:
   a plurality of piezoelectric elements, each being aligned in a longitudinal direction;
   an electrode formed on a first surface of each of the plurality of piezoelectric elements;
   a wiring member configured to be joined with the electrode and electrically connected with the electrode;
   a recess provided at a joining area on the wiring member, wherein the wiring member is joined with the electrode at the joining area; and a dematching layer provided on a second surface of each of the plurality of piezoelectric elements, each second surface faces the first surface and is opposite to the first surface of on which the electrode and the wiring member are joined.

6. A processing method of an ultrasonic transducer module, the method comprising:
joining an electrode formed on a first surface of individual piezoelectric elements to a wiring member electrically connected with the electrode,
wherein each of the individual piezoelectric elements being aligned in a longitudinal direction, and the wiring member including a recess provided at a joining area on the wiring member, wherein the wiring member is joined with the electrode at the joining area; and
forming a dematching layer on a second surface of the individual piezoelectric elements, the second surface faces the first surface and is opposite to the first surface on which the electrode and the wiring member are joined.

7. The method according to claim 6, wherein the joining comprises joining the electrode and the wiring member by one of an electrolytic plating method or a molten solder method.

* * * * *